United States Patent [19]

Kennedy et al.

[11] Patent Number: 4,851,554

[45] Date of Patent: * Jul. 25, 1989

[54] CERTAIN 3-SUBSTITUTED 2-ALKYL BENZOFURAN DERIVATIVES

[75] Inventors: Thomas P. Kennedy, Memphis; George W. Kabalka, Knoxville, both of Tenn.

[73] Assignee: University of Tennessee Research Corporation, Knoxville, Tenn.

[*] Notice: The portion of the term of this patent subsequent to Feb. 28, 2006 has been disclaimed.

[21] Appl. No.: 103,484

[22] Filed: Sep. 30, 1987

Related U.S. Application Data

[63] Continuation-in-part of Ser. No. 35,049, Apr. 6, 1987, Pat. No. 4,806,663.

[51] Int. Cl.$^4$ .................................... C07D 307/81
[52] U.S. Cl. .................................... 549/471; 549/469; 544/153; 544/376; 546/196; 548/525
[58] Field of Search .................... 549/469, 471; 544/153, 544/376; 546/196; 548/525

[56] References Cited

U.S. PATENT DOCUMENTS

| | | | |
|---|---|---|---|
| 3,248,401 | 4/1966 | Tondeur et al. | 549/468 |
| 3,627,763 | 12/1971 | Jaeggi et al. | 260/247.7 |
| 3,810,991 | 5/1974 | Binon et al. | 424/263 |
| 3,818,035 | 6/1974 | Binon | 260/309.6 |
| 3,891,648 | 6/1975 | Descamps et al. | 260/268 BC |
| 3,917,600 | 11/1975 | Descamps et al. | 260/268 |
| 3,920,707 | 11/1975 | Descamps et al. | 260/346.2 R |
| 3,929,836 | 12/1975 | Fothergill et al. | 260/346.2 R |
| 3,931,240 | 1/1976 | Binon et al. | 260/346.2 R |
| 3,972,900 | 8/1976 | Fothergill et al. | 260/346.2 R |
| 4,007,204 | 2/1977 | Descamps et al. | 260/330.5 |
| 4,485,112 | 11/1984 | Pestellini et al. | 424/285 |

OTHER PUBLICATIONS

Fieser et al., Advanced Org. Chem., Reinhold Pub., pp. 441–443 (1961).

Pollak et al., American J. of Medicine, 76, pp. 935–939, (1984).

Title: Medical Intelligence Drug Therapy—Amiodarone; Author: Jay W. Mason; Publication: The New England Journal of Medicine, vol. 316, No. 8, Feb. 19, 1987.

Spectroscopic Studies of Cutaneous Photosensitizing Agents—IX, A Spin Trapping Study of the Photolysis of Amiodarone, Anson S. W. Li and Colin F. Chingnell, *Photochemistry and Photobiology*, vol. 45, No. 2, pp. 191–197, Feb. 1987.

The Effect on Atrial and Ventricular Intracellular Potentials, and Other Pharmacological Actions of L9146, a Non-Halogenated Benzo(b)Thiophene Related to Amiodarone, E. M. Vaughan Williams, L. Salako and H. Witting. Caardiovascular Research, 1977, 11, 187–197.

*Primary Examiner*—Mary C. Lee
*Assistant Examiner*—Bernard I. Dentz
*Attorney, Agent, or Firm*—Luedeka, Hodges & Neely

[57] ABSTRACT

The disclosure relates to compounds of the formula

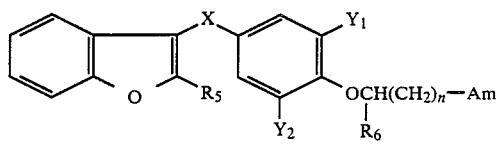

and pharmaceutically acceptable addition salts thereof wherein X represents a single, direct bond or a substituted or unsubstituted alkylene chain containing 1 to 4 carbon atoms, wherein $R_5$ is a lower alkyl group, wherein $R_6$ is either hydrogen or methyl, wherein Am is selected from the class consisting of amino, lower mono and dialkylamino, piperidino, piperazino, N-lower alkyl piperazino, pyrrolidino, and morpholino groups, wherein $Y_1$ and $Y_2$ are identical and are hydrogen, a halogen, methyl or ethyl and n is an integer in the range of 1–5.

5 Claims, No Drawings

CERTAIN 3-SUBSTITUTED 2-ALKYL BENZOFURAN DERIVATIVES

The U.S. Government has rights in the invention disclosed and claimed in this application pursuant to NIOSH Grant No. R01-OH02264-01.

The present application is a continuation-in-part of application Ser. No. 035,049, filed now Apr. 6, 1987, now U.S. Pat. No. 4,806,663 which is incorporated herein by reference.

The invention relates to compounds having pharmacological activity and more particularly relates to novel pharmacologically active 3-substituted 2-alkyl benzofuran derivatives, and methods for their preparation.

Compounds in accordance with the invention are represented by the general formula:

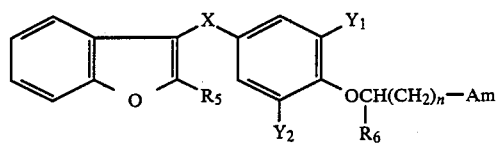

and pharmaceutically acceptable addition salts thereof wherein X represents a single, direct bond or a substituted or unsubstituted alkylene chain containing 1 to 4 carbon atoms, wherein $R_5$ is a lower alkyl group, wherein $R_6$ is either hydrogen or methyl, wherein Am is a group selected from the class consisting of amino, lower mono and dialkylamino, piperidino, piperizino, N-lower alkyl piperizino, pyrrolidino, and morpholino groups, wherein $Y_1$ and $Y_2$ are identical and are hydrogen, halogen, methyl or ethyl, and n is an integer in the range of 1-5.

The term "unsubstituted or substituted alkylene chain containing 1 to 4 carbon atoms" is intended, unless further defined, to designate a saturated aliphatic hydrocarbon chain of between 1 and 4 carbon atoms with or without one or more substituents. Substituents are limited to those which do not diminish the pharmacological activity of the copounds below a useful level and include branched or straight-chain alkyl or cycloalkyl groups, aryl groups, alkoxy groups, and ester substituents. "Lower alkyl" is intended to designate straight-chain, branched, or cyclic saturated aliphatic hydrocarbon groups containing 1-6 carbon atoms. "Lower mono and dialkylamino" refers to amino groups with one or two straight-chain, branched or cyclic saturated aliphatic hydrocarbon groups containing 1-6 carbon atoms. When two groups are present, they may be the same or different. Examples are methylamino, dimethylamino, ethylamino, diethylamino, n-propylamino, isopropylamino, and the like. Halogen, unless further defined, is intended to refer to fluorine, chlorine, bromine, and iodine.

Compounds in accordance with the invention are useful as vasodilators and as antiarrythmic agents. Preferred for this purpose are compounds of Formula I above wherein X represents the Formula 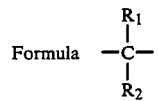

above wherein $R_1$ and/or $R_2$ are hydrogen, lower alkyl groups, groups with the Formula $-OR_3$ with $R_3$ being a lower alkyl group, or groups with the Formula 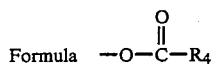

with $R_4$ being hydrogen or a lower alkyl group, $R_5$ is a lower alkyl group containing 1-4 carbon atoms, $R_6$ is hydrogen, Am is as defined above for Formula I, $Y_1$ and $Y_2$ are identical and are hydrogen, bromine, iodine, or methyl, and n is in the range of 1-3. Particularly preferred are compounds wherein X is

wherein $R_2$ is hydrogen and $R_1$ is hydrogen, or $-OR_3$ with $R_3$ being a lower alkyl group, or $R_1$ is

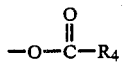

with $R_4$ being hydrogen or a lower alkyl group, $R_5$ is butyl, $R_6$ is hydrogen, Am is amino or lower mono and dialkyl amino, $Y_1$ and $Y_2$ are identical and are hydrogen, bromine, iodine, or methyl and n is an integer in the range of 1-3. Most preferably, X is

wherein $R_2$ is hydrogen and $R_1$ is hydrogen or $-OR_3$ with $R_3$ being a lower alkyl group containing between 1 and 4 carbon atoms, or $R_1$ is

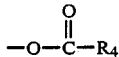

with $R_4$ being hydrogen or a lower alkyl group containing 1 to 4 carbon atoms, $R_5$ is n-butyl, $R_6$ is hydrogen, Am is amino, ethylamino or diethylamino, $Y_1$ and $Y_2$ are either both hydrogen, both iodine, or both methyl, and n is 1. Of the most preferred compounds, compounds where $R_1$ and $R_2$ are both hydrogen are particularly desirable.

Compounds of Formula I in which $R_6$ is hydrogen are prepared by first condensing an alkali metal salt of a compound represented by Formula II below in which X, $R_5$, $Y_1$ and $Y_2$ have the same meanings as in Formula I with a dibromoalkane represented by Formula III in which $R_6$ is hydrogen and n is 1-5 in an inert organic medium such as dimethyl formamide.

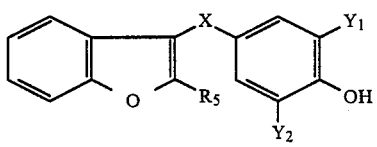

-continued

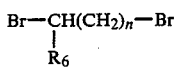
III

The resulting bromoalkyloxy-substituted compounds of Formula IV are condensed with an amine of the Formula V in which Am has the same meaning as in Formula I in an inert solvent such as benzene to produce the Formula I compounds.

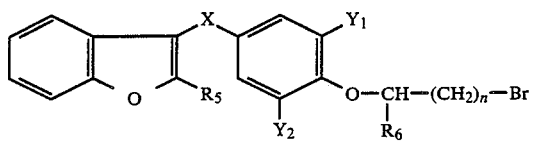
IV

H—Am   V

Alternatively, when Am does not represent a secondary amine and $R_6$ is either hydrogen or methyl, an alkali metal salt of a compound of Formula II can be condensed with an amine represented by Formula VI in which Z is a halogen atom to produce of Formula I compounds.

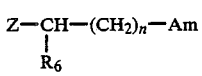
VI

The compounds represented by Formula II can be synthesized by a number of reaction routes. As will become more apparent hereinafter, many of such compounds can be prepared by reduction of or reduction and subsequent reaction of a ketone intermediate represented by Formula VII wherein A is a single direct bond or a substituted or unsubstituted alkalene chain containing 1-3 carbon atoms in the chain and $R_5$, $Y_1$, and $Y_2$ are as defined in Formula I.

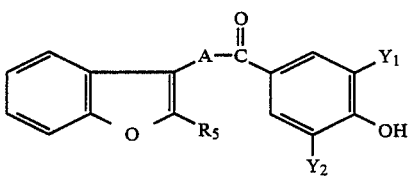
VII

When A is a single, direct bond, Formula VII ketones are known intermediates and are disclosed in U.S. Pat. Nos. 3,248,401 and 3,920,707, which are incorporated herein by reference.

When A represents a substituted or unsubstituted alkalene chain containing 0-3 carbon atoms, the ketone intermediates represented by Formula VII can be prepared by Friedel-Crafts acylation of a 2,6-substituted anisole of Formula IX with an acid chloride of Formula VIII wherein m represents an integer of 0-3 and $R_7$ and $R_8$ represent the same entities as $R_1$ and $R_2$ or precursors thereof followed by demethylation of the anisole with pyridine hydrochloride.

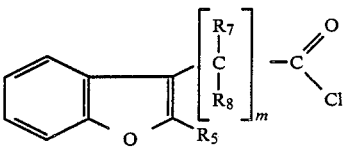
VIII

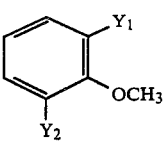
IX

The acid chlorides of Formula VIII can be prepared from 3-carboxy-2-alkyl benzofurans of the Formula X by reaction with an alkene Grignard reagent of Formula XI wherein o is 0-2 and $R_7$ and $R_8$ are defined as in Formula VIII in the presence of $CdCl_2$ to result in the formation of the secondary alcohols of Formula XII.

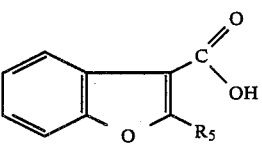
X

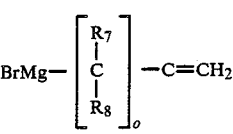
XI

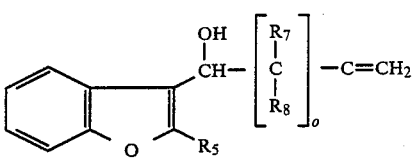
XII

Formula XII alcohols can be dehydrated to the corresponding alkenes of Formula XIII below by reaction with sulfonyl chloride in pyridine followed by reaction with lithium triethyl borohydride. Formula XIII alkene substituted benzofuran compounds are converted to acid chlorides of Formula VIII by ozination in the presence of zinc and oxidation of the resulting aldehyde or Formula XIV to the carboxylic acid employing potassium permanganate (cold) followed by reaction with sulfonyl chloride.

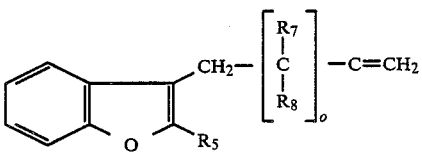
XIII

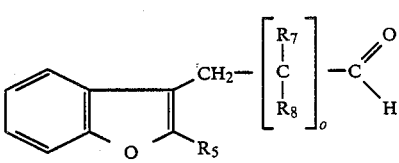
XIV

When X is a single direct bond, compounds of Formula I are prepared by first reacting a compound of Formula XV with $Y_1$ and $Y_2$ as defined in Formula I with ethyl bromoacetate in acetone in the presence of $K_2CO_3$ to form a compound of Formula XVI. Formula XVI compounds are converted to the compounds of Formula XVII by Perkin condensation in the presence of acetic anhydride and sodium acetate followed by the conversion of the ester group to $R_5$ groups. Demethylation of the substituted anisole moiety yields compounds of Formula II wherein X is a single, direct bond which can be employed as previously discussed to prepare Formula I compounds.

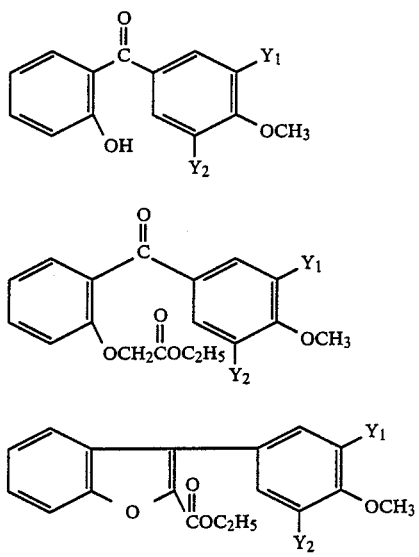

Compounds of Formula XV can be prepared by FriedelCrafts acylation of the substituted anisoles of Formula IX with salicyloyl chloride.

The particularly preferred compounds of Formula I described above wherein X is

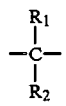

and $R_2$ is hydrogen and $R_2$ is hydrogen or $-OR_3$ with $R_3$ being a lower alkyl group or

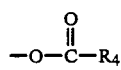

with $R_4$ being hydrogen or a lower alkyl group are advantageously prepared by way of an alcohol intermediate which is produced by reducing a ketone of the formula:

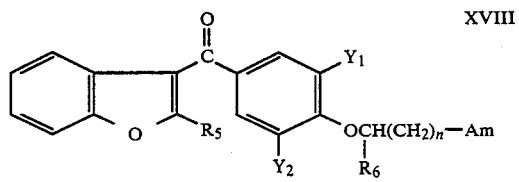

with $R_4$, $R_5$, $R_6$, $Y_1$ and $Y_2$, and n as defined for Formula I. Formula XVII ketones are known and procedures for their synthesis are described in U.S. Pat. Nos. 3,248,401 and 3,920,707, the disclosures of which are incorporated herein by reference. To produce compounds according to Formula I wherein $Y_1$ and $Y_2$ are identical halogens, reduction of the compounds of Formula XVIII with $Y_1$ and $Y_2$ being halogens is performed under conditions which reduce the ketone group to the alcohol without otherwise affecting the molecule. A reducing system employing sodium borohydride in a tetrahydrofuran-methanol mixture (10:1 v/v) at approximately 0° C. produces high yields of the alcohol represented by Formula XIX:

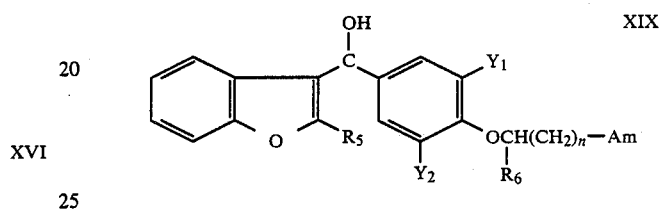

To prepare compounds of the invention wherein $Y_1$ and $Y_2$ are both hydrogen, both methyl, or both ethyl, the ketones of the Formula XIV wherein $Y_1$ and $Y_2$ are both hydrogen, both methyl or both ethyl are similarly reduced to produce the alcohol intermediate shown in Formula XX. Alternatively, to produce the compounds where $Y_1$ and $Y_2$ are both hydrogen, reduction of Formula XVIII compounds wherein $Y_1$ and $Y_2$ are both halogens can be performed employing a reduction system which reduces the ketone group to the alcohol while also dehalogenating the benzene ring to produce Formula XX alcohols. Sodium borohydride in methanol in the presence of a $PdCl_2$ catalyst at 20° C. is a preferred reduction system to achieve both reduction and dehalogenation.

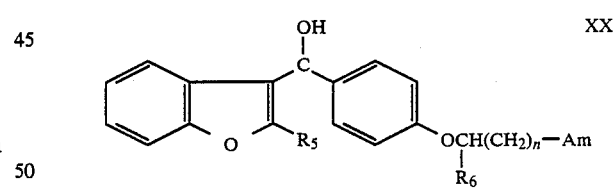

Compounds of Formula I wherein X is

and $R_1$ (and $R_2$) is hydrogen are produced from the intermediates of Formulas XIX and XX by further reduction at the alcohol group. Compounds of Formula XIX ($Y_1$ and $Y_2$ are both halogen,s methyl or ethyl) or XX ($Y_1$ and $Y_2$ are both hydrogen), when reacted in a suitable solvent at 0° C. with sodium borohydride in trifluoroacetic acid produce compounds of Formulas XXI and XXII, respectively.

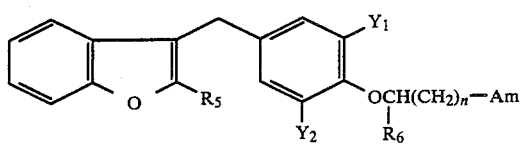

XXI

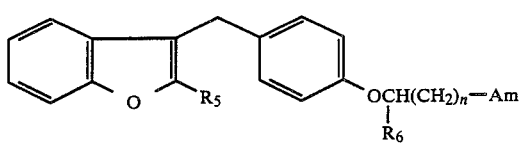

XXII

The alcohols of Formulas XIX and XX are also employed as intermediates to produce compounds wherein X is

and $R_2$ is hydrogen and $R_1$ is $-OR_3$ being a lower alkyl group. A Williamson synthesis whereby the alcohols or Formula XIX or XVII are converted to the corresponding alkoxide and reacted with an alkyl halide of the Formula $R_3X$ is used to produce the ethers represented by Formulas XXIII ($Y_1$ and $Y_2$ are both halogens, methyl or ethyl) and XXIV ($Y_1$ and $Y_2$ are both hydrogen).

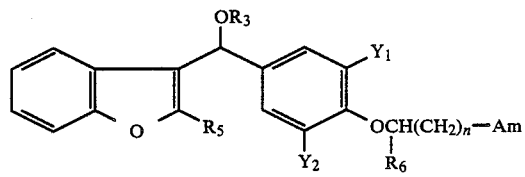

XXIII

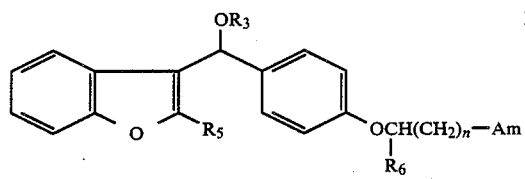

XXIV

To produce the compounds of Formula I wherein X is

and $R_1$ is

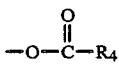

($R_2$ is hydrogen), the alcohols of Formulas XIX and XX are esterified. Acyl halides of the

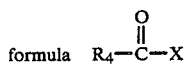

formula $R_4-\overset{\overset{O}{\|}}{C}-X$ can be reacted with the alcohols of Formulas XIX or XX, respectively, preferably in the presence of a solvent capable of acting as an acid scavenger, e.g., pryridine, to produce compounds of Formulas XXV (halogenated) ($Y_1$ and $Y_2$ are both halogen, methyl or ethyl) or XXVI ($Y_1$ and $Y_2$ are both hydrogen), respectively:

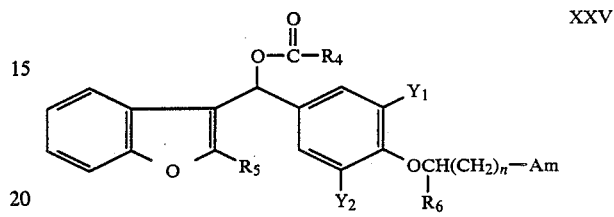

XXV

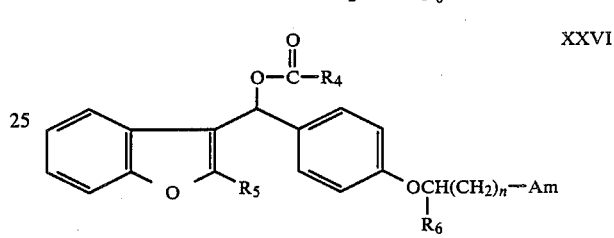

XXVI

The compounds of Formula I react to form acid addition salts with pharmaceutically acceptable acids, for example, with inorganic acids, such as hydrochloric acid, hydrobromic acid, sulphuric acid and phosphoric acid and with organic acids such as acetic acid, tartaric acid, maleic acid, citric acid and toluenesulfonic acid.

The compounds of the Formula I above and the salts thereof are useful in treating arrhythmic conditions and conditions for which treatment with a vasodilator is indicated. The novel pharmaceutically active agents provided by the present invention can be administered in pharmaceutical dosage forms, internally, for example, parenterally or enterally with dosage adjusted to fit the exigencies of the therapeutic situation. The pharmaceutical dosage forms are prepared by incorporating the active ingredient in conventional liquid or solid vehicles to thereby provide emulsions, suspensions, tablets, capsules, powders and the like according to acceptable pharmaceutical practices. A wide variety of carriers or diluents as well as emulsifying agents, dispersing agents and other pharmaceutically acceptable adjuvants can be incorporated in the pharmaceutical dosage forms.

The following examples are offered to illustrate the invention and are not intended to be limiting.

EXAMPLE I

Preparation of (2-n-butyl-3-benzofuranyl) [4-[2-(diethylamino)ethoxyl]-3,5-diiodophenyl] methanol.

One 1 mmole (645 mg) of the ketone (2-n-butyl-3-benzofuranyl) [4-[2-(diethylamino)ethoxyl]-3,5-diiodophenyl] methanone is dissolved in 30 ml of THF:MeOH (10:1 v/v). Sodium borohydride (1.2 mmole, 45.42 mg) is added to the solution and the mixture is stirred and maintained at a temperature of 0° C. until the starting material is consumed (~15 minutes). Excess borohydride is destroyed by the dropwise addition of water (0.5 ml). Volatile components are removed under reduced pressure (roto-evaporator). Water is added to the residue (~10 ml) followed by the addition of methylene chloride (~10 ml). The methylene chloride layer is separated from the aqueous phase and is dried over anydrous sodium sulfate. The methylene chloride solvent is removed under reduced pressure and the product is purified by column chromatography (silica gel support using methylene chloride) and is recovered by reduced pressure evaporation of the methylene chloride. The yield of the product, m.p. 106°–107° C., is >50% of theoretical. (The m.p. of the hydrochloride salt is 143°–145° C.)

EXAMPLE II

Preparation of (2-n-butyl-3-benzofuranyl) [4-[2-(diethylamino)ethoxyl]-phenyl] methanol One mmole (645 mg) of the ketone, (2-n-butyl-3-benzofuranyl) [4-[2-(diethylamino)ethoxyl]-3,5-diiodophenyl] methanone is dissolved in 10 ml of methanol. Palladium dichloride (2 mmole, 354 mg) is added and the mixture is agitated to suspend the palladium dichloride. The temperature of the mixture is adjusted to 20° C. Sodium borohydride (10 mmole, 379 mg) is added and stirring is continued until reaction is complete (~1 hour). The palladium dichloride is removed by filtration and water is added to the filtrate. An ether extraction is performed and the product is removed from the ether phase by evaporation under reduced pressure. The produce is purified by chromatography (silica gel using methylene chloride) and results in >50% yield of the product, m.p. 203° C. (decomposes).

EXAMPLE III

Preparation of (2-n-butyl-3-benzofuranyl) [4-[2-(diethylamino)ethoxyl]-3,5-diiodophenyl] methane One mmole (647 mg) of the alcohol as prepared in EXAMPLE I is dissolved in methylene chloride (5 ml). Sodium borohydride (38 mg, 10 mmole) added to 10 ml of trifluoroacetic acid and the mixture is cooled to 0° C. The methylene chloride solution is added slowly to the trifluoacetic acid solution and the mixture stirred for 30 minutes at 0° C. Excess borohydride is destroyed by the dropwise addition of water (0.5 ml). Volatile components are removed under reduced pressure (rotorevaporator). Water is added to the residue (25 ml) followed by the addition of methylene chloride (25 ml). The methylene chloride layer is separated, washed twice with 25 ml of 5% aqueous sodium hydroxide and 25 ml of water. The methylene chloride solution is dried over sodium sulphate and then passed through a short (~5 cm) basic alumina column. Evaporation of the solvent yields the product, m.p. 80°–81° C., in >70% yield. (The m.p. of the hydrochloride salt is 119°–121° C.)

EXAMPLE IV

Preparation of methoxy (2-n-butyl-3-benzofuranyl) [4-[2-(diethylamino)ethoxyl]-3,5-diiodophenyl] methane One mmole (647 mg) of the alcohol as prepared in EXAMPLE I is dissolved in 10 ml of THF. The solution is cooled to −78° C. and lithium diisopropylamide in cyclohexane (1.1 mmole, 0.73 ml of a 1.5 M solution) is slowly added. Methyl iodide (1.2 mmole, 0.17 g) is added and the mixture permitted to warm to room temperature (~30 minutes). The volatile components are removed under reduced pressure (rotoevaporator) and the residue is dissolved in methylene chloride. The methylene chloride solution is dried over anhydrous sodium sulfate and is purified by passing the solution through silica gel column as in EXAMPLE I. The product, m.p. 96°–98° C., is obtained upon evaporation of the solvent in a theoretical yield of >90%.

EXAMPLE V

Preparation of (2-n-butyl-3-benzofuranyl) [4-[2-(diethylamino)ethoxyl]-3,5-diiodophenyl] methyl pivalate One mmole (647 mg) of the alcohol as prepared in EXAMPLE I is dissolved in pyridine (4 ml). Excess pivaloyl chloride (5 mmole, 605 mg) is added to the pyridine solution and the mixture heated to 65° C. until the starting alcohol is completely consumed (approximately 12 hours). Volatile materials are removed under reduced pressure (rotoevaporator). The residue is dissolved in methylene chloride and the methylene chloride solution washed twice with 25 ml of 5% aqueous sodium hydroxide and once with 25 ml of water. The methylene chloride solution is dried over sodium sulfate and then passed through a short (~5 cm) basic alumina column. Evaporation of the solvent yields the product in >90% yield. (The m.p. of the hydrochloride salt is 108°–110° C.)

What is claimed is:

1. A compound of the formula:

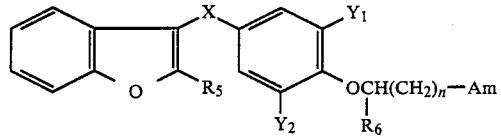

and pharmaceutically acceptable addition salts thereof wherein X represents a single, direct bond or a substituted or unsubstituted alkylene chain containing 1 to 4 carbon atoms, where such substituents are one or more members selected from the group consisting of branched or straight-chain alkyl, cycloalkyl, aryl, alkoxy, and

with $R_4$ being hydrogen or lower alkyl, wherein $R_5$ is a lower alkyl group, wherein $R_6$ is either hydrogen or methyl, wherein Am is a group selected from the class consisting of amino, lower mono and dialkylamino, piperidino, piperazine, N-lower alkyl piperazino, pyrrolidino, and morpholino groups, wherein $Y_1$ and $Y_2$ are identical and are selected from the class consisting of hydrogen, halogen, methyl and ethyl and n is an integer in the range of 1–5.

2. A compound as set forth in claim 1 wherein X represents an alkylene chain having the formula 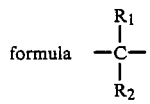

wherein either $R_1$ or $R_2$ is hydrogen and the other of $R_1$ or $R_2$ is selected from the class consisting of hydrogen, a group having the formula $-OR_3$ with $R_3$ being a lower alkyl group, and a group having the formula 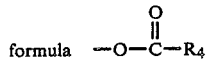

with $R_4$ being hydrogen or a lower alkyl group, $R_5$ is butyl, $R_6$ is hydrogen, Am is selected from the class consisting of amino and lower mono and dialkylamino and $Y_1$ $Y_2$ are identical and are selected from the class consisting of hydrogen, bromine, iodine, and methyl and n is an integer in the range of 1-3.

3. A compound as set forth in claim 2 wherein $R_2$ is hydrogen and $R_1$ is selected from the class consisting of hydrogen, a group having the formula $-OR_3$ with $R_3$ being a lower alkyl group, and a group having the formula 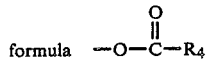

with $R_4$ being hydrogen or a lower alkyl group, $R_5$ is butyl, $R_6$ is hydrogen, Am is selected from the class consisting of amino, ethylamino, and dialkylamino, $Y_1$ and $Y_2$ are identical and are selected from the class consisting of hydrogen, iodine, and methyl and n is an integer in the range of 1-3.

4. A compound as set forth in claim 2 wherein $R_2$ is hydrogen and $R_1$ is selected from the class consisting of hydrogen, $-OR_3$ with $R_3$ being a lower alkyl group containing between 1 and 4 carbon atoms,

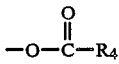

with $R_4$ being hydrogen or a lower alkyl containing 1-4 carbon atoms, $R_5$ is n-butyl, $R_6$ is hydrogen, Am is amino, ethylamino or diethylamino, $Y_1$ and $Y_2$ are identical and are selected from the class consisting of hydrogen, iodine, and methyl, and n is 1.

5. A compound as set forth in claim 4 wherein both $R_1$ and $R_2$ are hydrogen.

* * * * *

UNITED STATES PATENT AND TRADEMARK OFFICE
CERTIFICATE OF CORRECTION

PATENT NO. : 4,851,554
DATED : July 25, 1989
INVENTOR(S) : Thomas P. Kennedy and George W. Kabalka It is certified that error appears in the above-identified patent and that said Letters Patent is hereby corrected as shown below:

Col. 1, Line 44, "copounds" should be --compounds--.

Col. 3, Line 20, "H-Am V" should read --H-Am--.

Col. 4, Line 49, "or" should be --of--.

Col. 5, Line 39, "delCrafts" should read --del Crafts--.

Col. 6, line 63, "halogen,s" should be --halogens,--.

Col. 9, Line 46, "(rotor-" should read --(roto- --.

Col. 10, Line 56, "piperazine" should be --piperazino--.

Signed and Sealed this

Twenty-third Day of October, 1990

*Attest:*

HARRY F. MANBECK, JR.

*Attesting Officer*      *Commissioner of Patents and Trademarks*